United States Patent
Bennett et al.

(10) Patent No.: US 6,993,808 B1
(45) Date of Patent: Feb. 7, 2006

(54) ADJUSTABLE HINGES FOR ORTHOPEDIC SPLINTS

(75) Inventors: John E. Bennett, Rancho Palos Verdes, CA (US); Willis C. Bradley, Gardena, CA (US)

(73) Assignee: Lenjoy Medical Engineering, Inc., Gardena, CA (US)

( * ) Notice: Subject to any disclaimer, the term of this patent is extended or adjusted under 35 U.S.C. 154(b) by 0 days.

(21) Appl. No.: 09/664,085

(22) Filed: Sep. 18, 2000

(51) Int. Cl.
*E05D 11/10* (2006.01)

(52) U.S. Cl. .............................. 16/334; 16/321; 602/16
(58) Field of Classification Search ................. 16/334, 16/321, 324, 333, 319; 602/16, 5
See application file for complete search history.

(56) References Cited

U.S. PATENT DOCUMENTS

| | | | | |
|---|---|---|---|---|
| 4,982,732 A | * | 1/1991 | Morris | 602/16 |
| 5,460,599 A | * | 10/1995 | Davis et al. | 602/16 |
| 5,814,000 A | * | 9/1998 | Kilbey | 602/16 |
| 5,873,847 A | * | 2/1999 | Bennett et al. | 602/16 |
| 5,938,629 A | * | 8/1999 | Bloedau | 602/16 |
| 5,997,493 A | * | 12/1999 | Young | 602/16 |
| 6,004,283 A | * | 12/1999 | Young | 602/16 |
| 6,203,511 B1 | * | 3/2001 | Johnson et al. | 602/16 |

* cited by examiner

*Primary Examiner*—Anthony Knight
*Assistant Examiner*—Doug Hutton
(74) *Attorney, Agent, or Firm*—Law Offices of Natan Epstein

(57) ABSTRACT

A hinge for an orthopedic splint has two plates hinged for pivotal movement relative to each other and a detent engageable for locking the plates at a selected angle to each other, and a spring urging the detent into engagement. The detent is protected in a recessed guideway against operation with the unaided hand to discourage tampering with the splint settings by the patient fitted with same, but is retractable with a pointed tool inserted in the recess or a removable screw threaded in the detent as a finger hold. The screw may also pass through the detent and if tightened against an underlying plate keeps the detent disengaged to facilitate adjustment of the splint. The hinge allows left and right hand angular settings of the splint to either side of a zero angle for ambidextrous use of the splint, and radial tabs with directional markings are provided as visual indicators of the angular setting of the splint hinge.

50 Claims, 4 Drawing Sheets

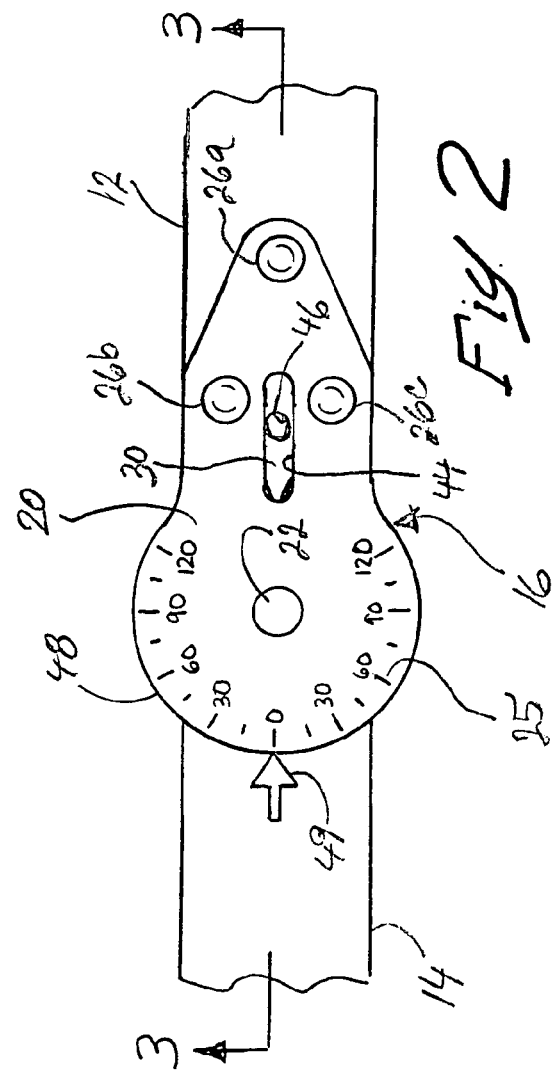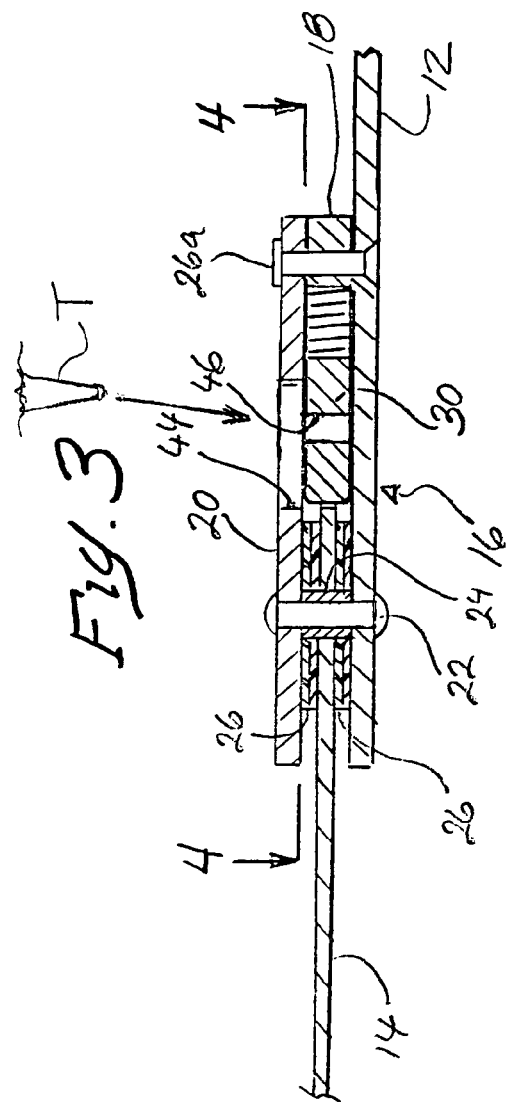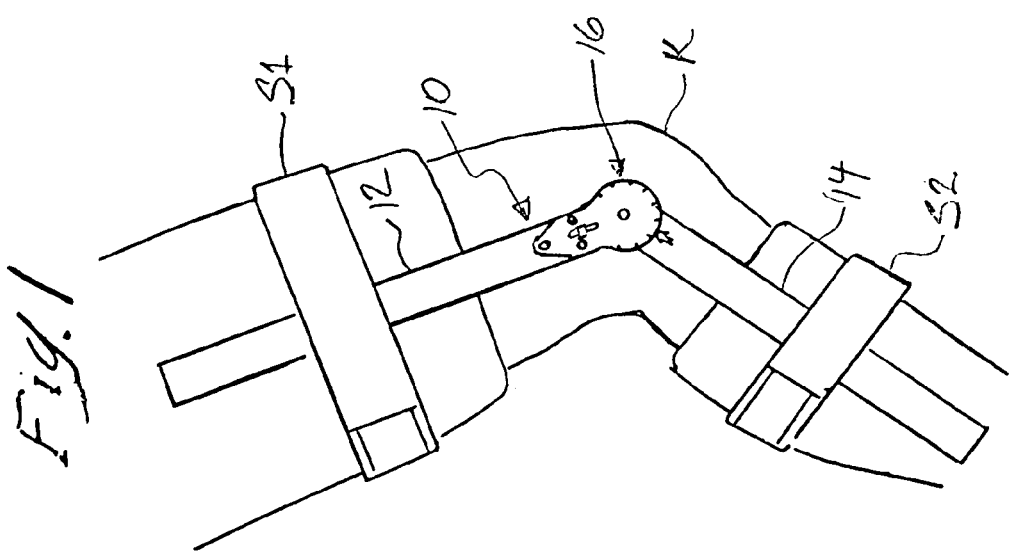

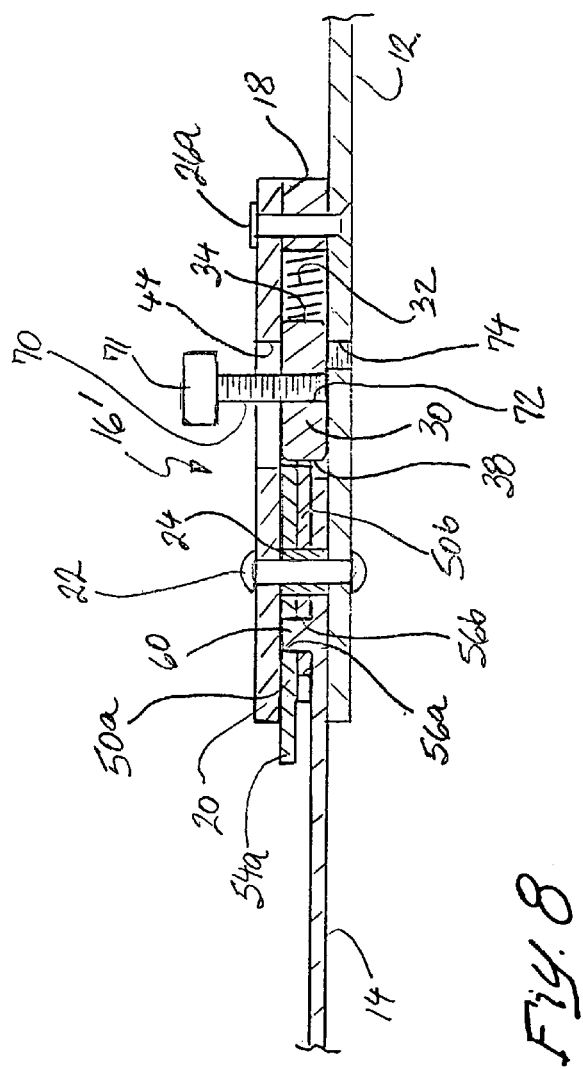
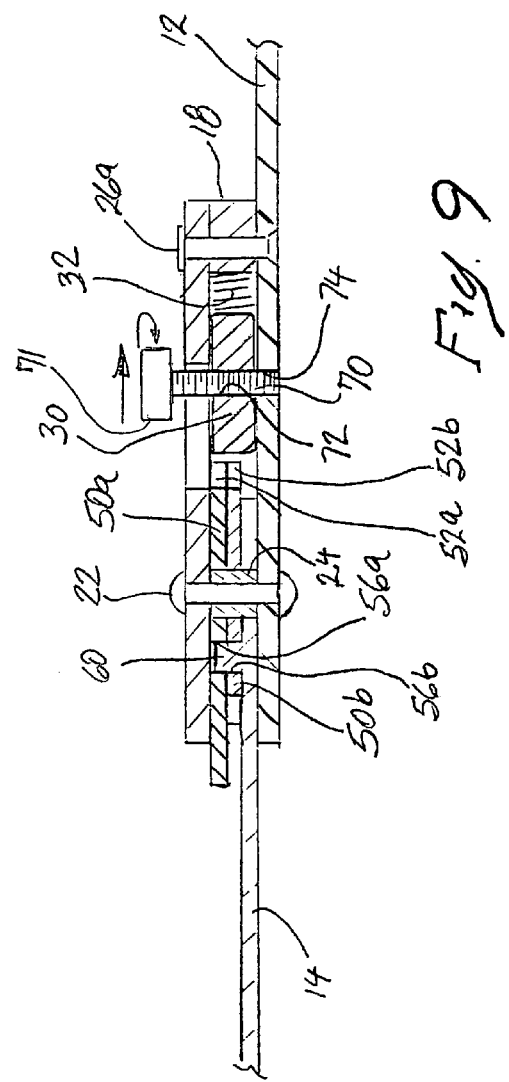

ADJUSTABLE HINGES FOR ORTHOPEDIC SPLINTS

BACKGROUND OF THE INVENTION

1. Field of the Invention

This invention pertains to the field of hinged orthopedic splints and braces of the type applied across the joint of a limb such as a knee or elbow for limiting movement of the joint for therapeutic purposes, and is more particularly directed to certain improvements in the hinge for such splints.

2. Background of the Invention

Knee and elbow splints or braces typically have an upper plate and a lower plate connected to each other by a hinge such that, when the upper plate is attached to the limb above the joint and the lower plate to the limb below the joint, the patient may flex the limb at the joint. Many such splints are known and are commonly used in the course of orthopedic rehabilitation. It is also known to provide splints with adjustable hinges which enable a therapist to set limits to the arc of movement of the splint and hence of the patient's joint, as may be required by the patient's condition and the course of therapy. One general class of knee brace in current use has a detent movable on an upper plate into and out of engagement with a toothed or serrated edge on a lower plate. Within this class of splints there are two types. In the first type the toothed edge may be fixed on one plate so as to lock the two plates in a selectable relative angular relationship, i.e., the two plates are fixed at a desired angle selected from a range of possible angular relationships. Once so fixed the two plates are not movable and the patient cannot flex the joint while wearing the splint. In the second type of splint within this class one or more toothed edges are adjustable on one plate enabling a variable range of movement to be set for the hinge. For example, two toothed elements are movable on the upper plate, such as two rotatable disks each with a toothed edge and a stop engageable by the lower plate. Angular movement of the lower plate relative to the upper plate is confined to an angular range defined by the relative positioning of the two stops, which in turn are adjustably set by rotation of the disks to the desired positions, and are fixed in that position by a common detent movable on the upper plate. In both types of splints the relative angular positioning of the two is set or limited by a detent movable on one plate and adjustably engagable with some structure mounted on the other plate.

A continuing problem encountered in this class of splints is to provide for convenient adjustment of the splint's angular settings by a therapist while also making the splint's settings relatively resistant to tampering by the patient who may become impatient with the course of therapy and wish to reset the splint to suit his or her immediate comfort.

A second shortcoming encountered in currently available knee or elbow braces of the aforementioned class is that the hinge settings are right or left handed, thereby limiting a particular splint to application on a limb of corresponding handedness. A continuing need exists for adjustable splints having ambidextrous hinge settings so that a given splint may be used interchangeably on either a right hand or left hand limb.

BRIEF SUMMARY OF THE INVENTION

The present invention addresses the aforementioned shortcomings by providing certain improvements in adjustable knee braces. These improvements include a tamper resistant hinge detent configured to discourage tampering by the patient with the hinge settings, a detent lockable in either a retracted or an engaged position to facilitate range setting by a therapist when locked in a disengaged condition of the detent and before securing the detent when locked in its engaged position, and a bidirectional hinge to allow use of the splint on either left or right limbs.

In general, the improvements of this invention concern the class of orthopedic splints having an upper plate and a lower plate connected for pivotal movement, and a detent element supported on the upper plate and displaceable into and out of an engaged condition with a structure on the lower plate thereby to fix or limit relative angular movement between the two plates. The detent is spring biased towards its engaged condition and must be retracted out of engagement against the spring bias by manual effort applied by a therapist.

In a first form the invention the toothed edge may be fixed to the lower plate in which case the splint is fixed at a selected angular relationship of the upper and lower plates. In a second form of the invention, two movable toothed edges are supported on the upper plate, such as on two wheels independently rotatable on the upper plate. Both wheels are locked against rotation relative to the upper plate by engagement with the detent, and the lower plate is free to pivot between two stops, one stop located on each wheel. The angular range of the plates is set by adjusting the angular spacing between the stops by rotation of the wheels while the detent is disengaged.

In one improvement according to the present invention the splint has a cover assembly for protecting the detent element against displacement out of engagement by an unaided hand, and an aperture in the cover sized and disposed for admitting a pointed tool end into engagement with the detent for displacing the detent out of its engaged condition, so that tampering with the angular setting of the hinge by a patient wearing said orthopedic splint is discouraged.

In a presently preferred embodiment of the invention, the detent is displaceable in a guide way defined between the upper plate and the cover assembly, and a biasing spring is contained in the guide way. The spring may be a coil spring compressed between the cover assembly and the detent. The cover assembly may include a spacer which is mounted between the upper plate and cover plate and defining the guide way for the detent, and a cover plate applied over the spacer for containing the detent in the guide way. The access aperture may be a slot in the cover plate, the slot being aligned with a direction of displacement of the detent. The detent preferably has a tool end receptacle such as a hole or depression adapted to receive the pointed tool and thereby to facilitate positive engagement and displacement of the detent by means of the tool end. The access aperture is preferably sized and shaped so as to allow visual confirmation of detent engagement with the toothed element.

Typically, the detent is engageable with an arcuate toothed edge supported on the lower plate, and the pivotal movement of the two plates of the splint comprises an arc including a zero angle position situated at an intermediate location along the arc, such that the plates may be moved through substantial angular ranges on either side of the zero angle position. The zero angle position may be centered along the arc such that the plates may be pivoted through equal angular ranges on either side of the zero angle position. The zero angle position may be situated along the arc such that the two plates are aligned in a straight line when the hinge is set to the zero angle position. By providing for a range of angular movement of the hinge to one side or the other of the zero position, the splint may be applied to a right side or a left side of a limb, eliminating the need for special left handed or right handed splints. In another aspect of the invention the hinge has a locking element removably engageable for holding the detent out of its engaged condition to thereby facilitate application of the splint to a patient's limb with the hinge free to rotate through its full 240 degree arc of movement, so that the therapist can bend the splint quickly and easily to match the position of the patient's limb. That is, the splint angle can be easily adjusted to the angle of the patient's joint rather than having to reposition the patient's limb to fit the angle of the splint. Once the splint is applied and fastened to the limb, the detent locking element facilitates setting of the hinge angular range by holding the detent out of engagement while the range setting elements or wheels are properly positioned, after which the detent may be released into engagement with the range setting elements.

The locking element may be in threaded engagement with the detent, such as a screw engageable in a threaded screw hole defined in the detent, such that an end of the screw bears against the upper plate in a tightened condition of the screw, or is advanced into a hole in the upper plate, thereby to hold the detent against the spring bias in a disengaged condition.

The structure engaged by the detent to fix or limit relative angular movement between the two plates may be a toothed edge fixed on the lower plate, such that the two plates are fixed in a selected angular relationship in an engaged condition of the detent. Alternatively, the structure engaged by the detent may be a range setting assembly adjustable for limiting pivotal movement between the two plates to a greater or lesser arc in an engaged condition of the detent. The range setting assembly may comprise a pair of wheels turning concentrically with the pivotal movement of the plates, each of the wheels having a wheel edge engageable by said detent for locking the wheel relative to the upper plate, and a stop on each of the wheels operative for limiting pivotal movement of the lower plate relative to the upper plate, and a pin or equivalent stop element on the lower plate being disposed between the two stops on the wheels such that the range of relative pivotal movement of the plates may be set by the angular spacing between the two stops when the detent is engaged for locking the wheels against rotation relative to the upper plate.

These and other improvements, features and advantages of this invention will be better understood by turning to the following description of the preferred embodiments taken in conjunction with the accompanying drawings.

BRIEF DESCRIPTION OF THE DRAWINGS

FIG. 1 is a top plan view of a knee brace according to this invention applied to the outside of a knee joint of a patient's leg;

FIG. 2 is an enlarged top plan view of an ambidextrous hinge according to this invention, with the upper and lower plates of the splint shown in straight line zero angle alignment;

FIG. 3 is a cross-sectional view of the hinge taken along line 3—3 in FIG. 2;

FIG. 8 is a cross-sectional view showing the detent in engagement with the rotatable toothed wheels of the range setting assembly of the hinge and the detent locking screw threaded into the detent but disengaged from the upper plate; and FIG. 9 is a view as in FIG. 8 but showing the detent in a retracted position compressing the biasing spring, and the detent locking screw passing through a hole in the upper plate and inserted into a hole in the lower plate to lock the detent in a retracted condition against the bias of the compressed spring.

DETAILED DESCRIPTION OF THE PREFERRED EMBODIMENTS

Figure 4:
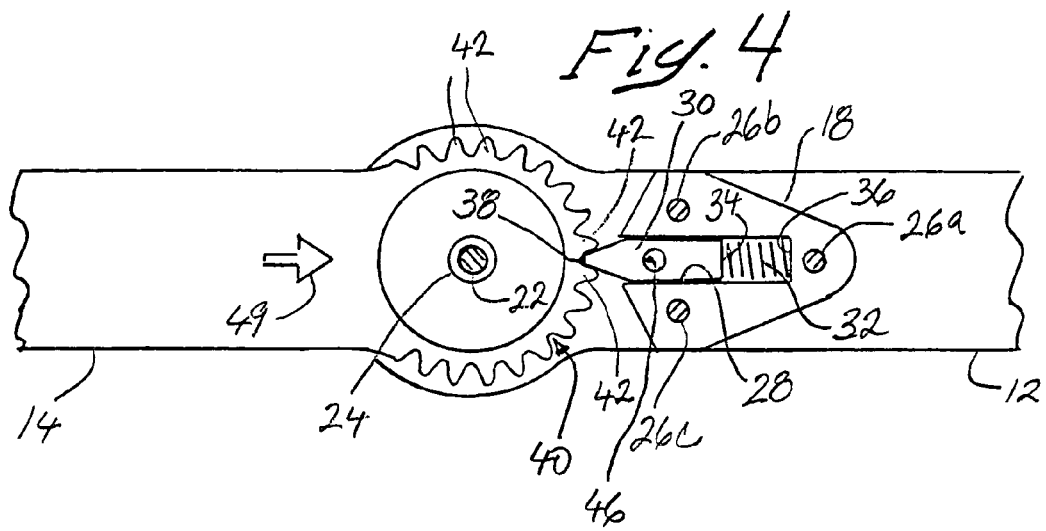
FIG. 4 is a view taken along lines 4—4 in FIG. 3 showing the interior of the hinge with the detent in engaged condition with the toothed edge of the lower plate, thereby locking the upper and lower plates against relative movement.

With reference to the drawings wherein like elements are designated by like numerals, FIG. 1 depicts an orthopedic splint or knee brace 10 applied to the knee joint K of a patient. The brace includes an upper plate 12 and a lower plate 14 connected to each other for pivotal movement by a hinge 16. The upper plate is attached to the thigh of the patient's leg by an upper strap S1 and the lower plate is similarly attached to the leg below the knee by a lower strap S2 so that the hinge 16 lies adjacent to and pivots with bending of the knee. Typically, two similar knee braces 10 are applied to the knee joint of the patient, one brace on the outside of the leg, as shown in FIG. 1, and an opposite second brace (hidden in FIG. 1) on the inside of the leg. The two braces are generally parallel to each other and provide lateral support to the knee joint while allowing flexing of the knee joint in a plane parallel to the planes of movement of the brace hinge 16. In the course of rehabilitation or other therapy it may be desirable to temporarily hold the knee at a particular fixed angle or to limit the range of movement of the knee to a given angular range. For this purpose the hinge of this invention is provided with an adjustable detent mechanism which will be described below.

FIGS. 2 through 5 illustrate a splint 10 of the first type with a hinge 16 which has a single toothed element fixed relative to one of the plates and engageable by the detent to fix the hinge and hence the plates 12, 14 at a selected angle within a range of angular movement of the hinge, and thereby immobilize the patient's leg at the selected angle. FIGS. 6 through 9 illustrate a hinge 16' for splints of the second type where the hinge has two toothed elements, both of which are movable relative to either the upper or lower plate, and are both immobilized relative to one of the plates by engagement with the detent so that the hinge can be set either at a fixed angle between the two plates or to allow relative pivotal movement of the upper and lower plates over an arbitrary, adjustable angular range, so that the patient's leg wearing a splint equipped with hinge 16' may bend at the knee but over a range limited by a setting of hinge 16' chosen by the therapist. While not shown in the drawings, hinge 16' is part of a splint 10' which is similar to splint 10 in FIG. 1 except that hinge 16' is substituted for hinge 16.

FIGS. 2 and 3 depict in greater detail the hinge 16. As best seen in FIG. 3 the upper plate 12 carries a cover assembly which includes a cover plate 20 and a spacer 18. The lower plate is pivotably connected to the upper plate by means of a pivot rivet or screw 22 which secures the cover plate 20 and the upper plate 12 to opposite sides of a pivot sleeve 24. The lower plate turns about the pivot sleeve 24 and is held between first and second pairs of washers 26 which reduce friction and facilitate relative pivotal movement between the upper and lower plates. The cover plate 20 is fixed to the upper plate by a rivet 26a which also passes through the spacer 18. The spacer 18 is further fastened to the upper plate by two additional rivets 26b,26c, seen in FIG. 2, which pass through the cover plate, spacer and upper plate in a manner similar to rivet 26a.

Figure 5:
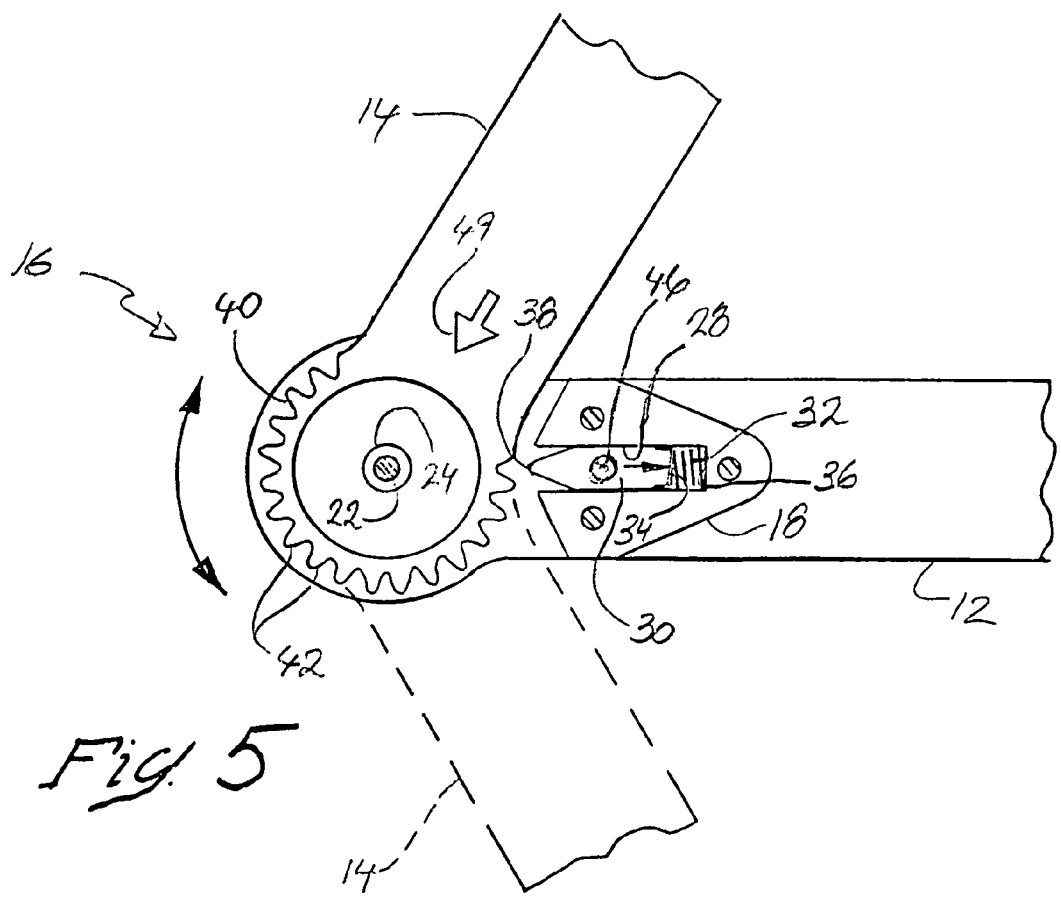
FIG. 5 is a view as in FIG. 4 showing the detent retracted against the bias spring to a disengaged position and depicting the angular range of movement of the lower plate between a solid lined position and a phantom lined position.

A detent 30 is captive in a guide way 28 defined in the spacer 18 as best seen in FIGS. 4 and 5. A bias spring 32 is compressed between the end 34 of the detent and the closed end 36 of the guide way 28. The cover plate 20, shown in FIG. 2 but removed in FIGS. 4 and 5 for clarity of illustration, holds both the detent and the bias spring in the guide way 28. The bias spring continuously urges the detent towards engagement with a circularly curved toothed edge 40 at the end of the lower plate 14. The detent has a pointed end 38 which fits between any adjacent pair of teeth 42 of the toothed edge 40, thereby interlocking the upper and lower plates 12, 14 against relative pivotal movement about the pivot sleeve 24 and pivot rivet or screw 22. In this condition the upper and lower plates of the brace are fixed at a particular angle to each other, and the knee of a patient wearing the brace is similarly fixed at this angle.

The toothed edge 40 extends along a circular arc of about 240 degrees centered on a straight line which passes through the pivot center of the hinge and also through the pointed end 38 of the detent. When the detent is engaged with the center of the toothed edge 40 as in FIG. 4 the upper plate 12 and the lower plate 14 are aligned in a straight line with each other. By retracting the detent to the disengaged condition of FIG. 5 the lower plate may be rotated 120 degrees left or 120 degrees right of the center or zero angle position of FIG. 4, as depicted by the solid lined and phantom lined positions, respectively, of the lower plate 14 in FIG. 5. Returning to FIG. 2, the top side of the cover plate 20 has a circularly curved edge 48 which is parallel to and overlies the toothed edge 40 of the lower plate. The edge 48 has a scale graduated in degrees of arc with a zero position at its center and graduations extending 120 degrees to each side of the zero position. A pointer 49 on the lower plate provides a reference for positioning the lower plate at a selected angle relative to the upper plate of the brace.

The brace of FIGS. 2 through 5 is ambidextrous, i.e., it may be used interchangeably on either a left or a right hand limb of a patient without modification or adjustment to the hinge mechanism. This is because a knee joint naturally flexes from a straight or zero angle position through an arc of some 120 degrees to a fully bent condition of the leg. The hinge of this invention provides for arcs of angular movement of 120 degrees to either side of the zero position of the hinge. Consequently, the brace 10 with hinge 16 can be applied interchangeably to either the inside or outside of a leg, and to either a left leg or a right leg of a patient. The hinge 16 will naturally rotate along the angular range on the appropriate side of the zero position of the hinge 16 according to the direction of motion of the knee joint to which it is applied, without need for attention on the part of the therapist. As a result, substantial savings may be realized in the manufacture of splints and also in the time and level of skill is required by therapies involving such splints.

Retraction of the detent 30 is accomplished by manually pushing or sliding the detent within the guide way 28 against the force of bias spring 32, compressing the bias spring as shown in FIG. 5 until the pointed end 38 of the detent is withdrawn from between the teeth 42 of the toothed edge, thereby freeing the lower plate 14 for rotation relative to the upper plate 12 about the pivot sleeve 24.

An access aperture in the form of slot 44 is cut in the cover plate 20 over the guide way 28 and oriented in the direction of movement of the detent 30. The slot 44 admits a narrow or pointed tool end to be introduced into contact and engagement with the detent 30, for the purpose of displacing the detent away from its engaged condition when adjustment of the brace angle setting is required. The slot 44 is shaped and sized, for example sufficiently elongated to expose the end of the detent in its engaged position and thus permit visual confirmation that the pointed end of the detent is satisfactorily engaged between the teeth of the toothed edge, as seen in FIG. 2. A receptacle in the form of a depression or hole 46 in detent 30 is aligned with access slot 44, as shown in FIG. 2. The receptacle 46 receives the narrow end of the tool and facilitates positive engagement between the tool and the detent while displacing the detent out of engagement and against the force of the bias spring 32. The access slot 44 effectively prevents access to the detent by an unaided hand, i.e. a hand unaided by a sufficiently narrow ended tool capable of passing through the slot 44 into the guide way 28. The detent is therefore recessed out of easy reach under the cover plate 20 and is protected against displacement away from its engaged condition by a patient's unaided hand, thereby discouraging tampering with the angular setting of the hinge 16 by a patient wearing the splint 10. The width of slot 44 is not critical, so long as it is sufficiently narrow to keep a finger from contacting and moving the detent 30. A slot width of $3/16^{ths}$ of an inch has been found satisfactory, and admits, for example, the pointed end T of a ball point pen or pencil, as shown in FIG. 3, or any other readily available implement which may be pressed into service by a therapist as a tool for adjusting the hinge angle setting of brace 10. Of course, in cases where tampering by the patient is not a concern, a post, pin, finger tab or equivalent structure extending above the cover plate 20 through slot 44 may be fitted in the receptacle 46 to provide a permanent or removable exteriorly accessible means for more conveniently moving the detent 30 out of engagement, such as screw 70 in FIG. 8. The screw 70 can be used by the therapist as a finger hold for pushing and disengaging the detent during splint installation. The screw 70 may then remain in place for subsequent detent engagement or disengagement, or it may be removed completely from the splint at the option of the therapist.

Turning now to FIGS. 6 through 9, hinge 16' has a detent 30 and detent cover assembly 20, 18 similar to those described above in connection with hinge 16 of FIGS. 2–5. The hinge 16' differs from hinge 16 in that the fixed toothed edge 40 of hinge 16 is replaced by a range adjustment assembly which includes two toothed wheels 50a, 50b, both rotatable on pivot sleeve 24 and thus concentrically with pivotal movement of the hinge. Each toothed wheel 50a,b has a circular toothed edge 52a, 52b extending about 240 degrees of arc about the respective wheel. An adjustment tab 54a, 54b extends radially from an untoothed portion of each wheel. Each wheel also has an arcuate slot 56*a*, 56*b* extending approximately 120 degrees of arc from an inside end 58 situated on a diameter line bisecting the toothed edge 52*a,b*, to an outside end 62. This diameter line also bisects the tab 54*a*, 54*b* of the wheel. The arcuate slots on the two wheels extend in opposite directions from their inside end 58. In a centered condition of the two wheels 50*a*,50*b* the detent 30 is aligned with the center of the toothed edge 52*a*,52*b*, as shown for wheel 50*a* in FIG. 6, so that the toothed edge of the wheel extends 120 degrees to either side of this center or zero position. It should be noted that the adjustment tab 54*a* is diametrically opposite to the center of the toothed edge 52*a* and in the centered condition of the wheel 50*a* the tab is also aligned with the lower plate 14 of the brace 10'. The toothed edge 52*b* is hidden directly under the toothed edge 52*a* in FIGS. 6 and 7 but is similar to edge 52*a*. The two wheels 50*a*, 50*b* are in fact interchangeable, and differ only in that one wheel is flipped over or turned upside down relative to the other on the pivot sleeve 24. Directional pointers L and R or similar directional indicia are provided on the tabs 54*a*, 54*b* in FIGS. 6 and 7 to guide the therapist when adjusting the angular constraints of the hinge. The directional indicia point in opposite directions of rotation to provide quick and easy identification of the two tabs.

A stop pin 60 is fixed to the lower plate 14 along a center line of the plate and extends through both arcuate slots 56*a*, 56*b*. The angular extent of rotation of each wheel 50*a*, 50*b* is therefore limited by the angular extent of the corresponding slot 56*a* or 56*b*. The range of angular movement of the hinge 16' is determined by the relative positions of both wheels 50*a*, 50*b* and the resulting degree of overlap of the two slots 56*a*, 56*b*. As seen in FIG. 8 the thickness of the detent 30 is sufficient to concurrently engage both toothed edges 52*a,b* and thereby lock both wheels 50*a,b* against rotation. The plates 12, 14 can also be locked at an angled position relative to each other by first placing the two plates at the desired angle, then turning the wheels 50*a,b* to superimpose the tabs 54*a,b* on the centerline of the lower plate thereby capturing the stop pin 60 between the ends 58 of the slots, and engaging the detent 30 to lock the wheels in this position. The hinge 16' may also be set for an arbitrary range of angular movement by positioning the two wheels such that the slots 56*a*, 56*b* overlap by the desired angular range between the slot ends 58, rotating the two wheels so as to position the overlapping slots 56*a*, 56*b* in the desired position relative to the upper plate 12 so as to set the desired maximum and minimum angles of the lower plate relative to the upper plate, and locking both wheels in this position by engaging the pointed end 38 of the detent with the toothed edges of both wheels. The minimum and maximum angles of rotation of the hinge may be read off the graduated scale 25 on cover 20 as indicated by the positions of tabs 54*a*, 54*b* relative to the scale. Arrow-type markings are situated on each tab to indicate their relative positioning to help avoid confusion on the part of the therapist.

Figure 6:
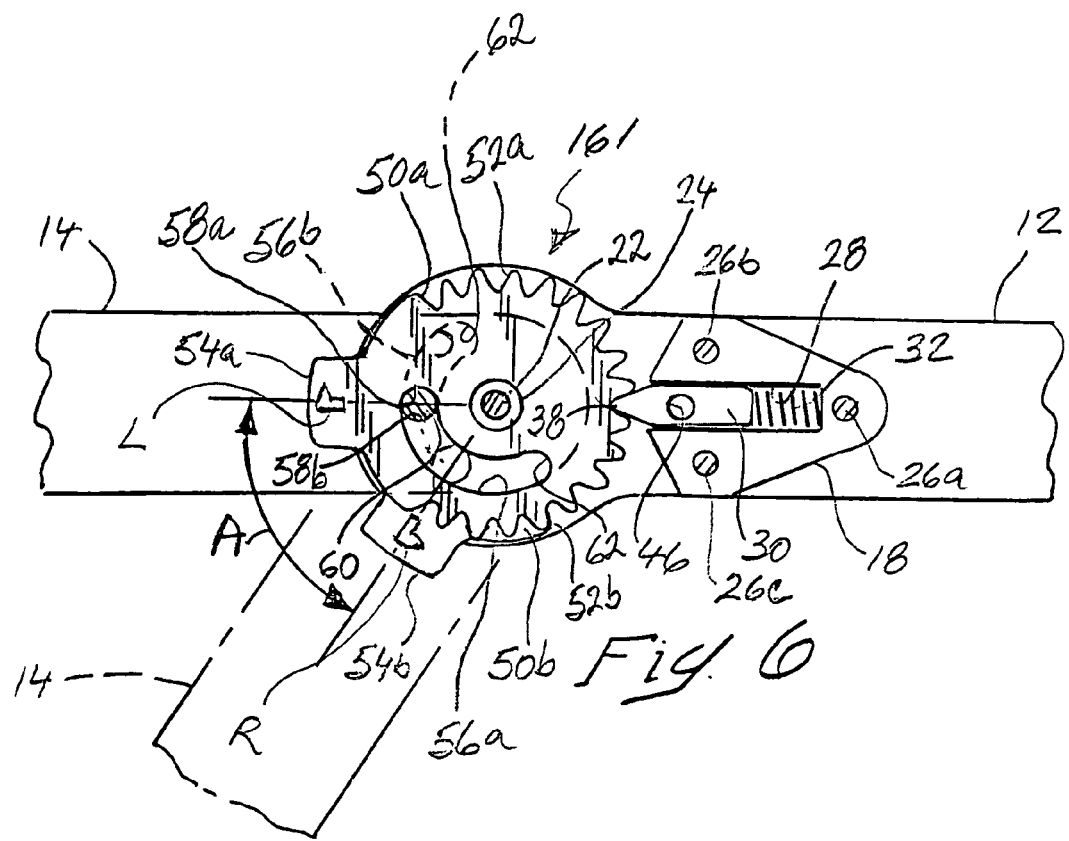
FIG. 6 shows a second type of ambidextrous hinge for limiting the pivotal movement between the upper plate and the lower plate of the splint to an adjustable angular range, the hinge being shown with the cover plate removed to expose the detent in engaged condition to limit the range of movement between solid and phantom lined positions of the lower plate on one side of a zero position of the hinge as indicated by angle A in the figure.
Figure 7:
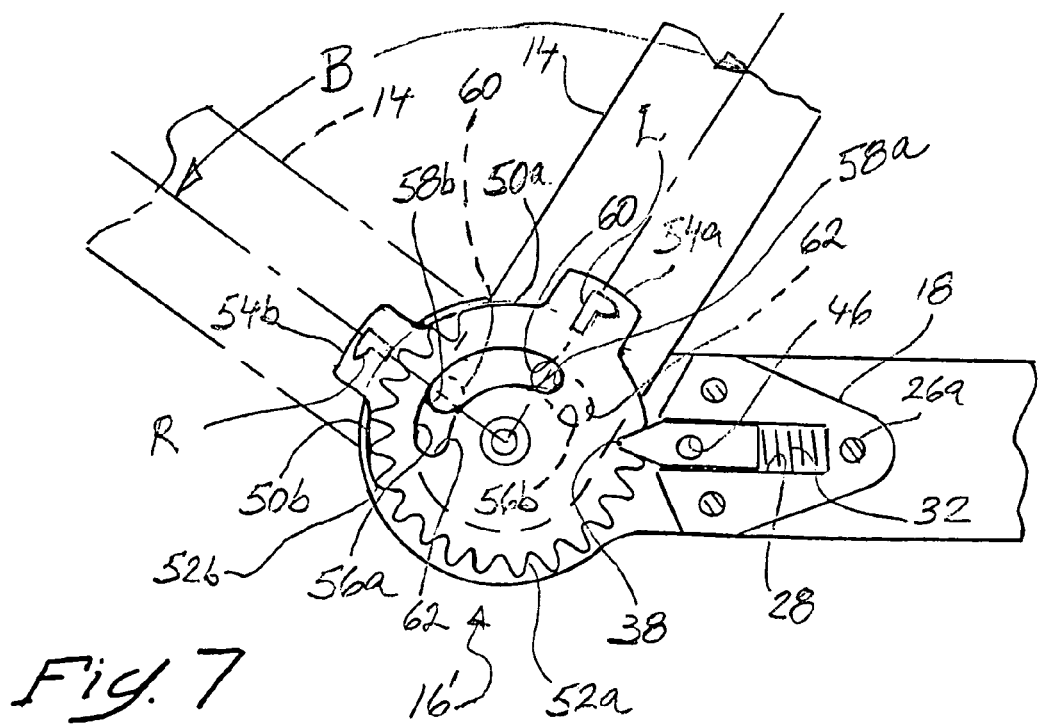
FIG. 7 shows the ambidextrous hinge of FIG. 6 set to a different angular range depicted by solid lined and phantom lined positions of the lower plate on the opposite side of the zero position of the hinge as indicated by angle B in the figure.

FIGS. 6 and 7 illustrate the ambidextrous capability of the hinge 16'. As explained in the preceding paragraph each toothed wheel 50*a,b* has a center position with a 120 degree angular range of the toothed edge on either side of the center position. Consequently the hinge 16' may be set for an arbitrary arc of movement of up to 120 degrees to either the left side or the right side of the center position. FIG. 6 depicts a setting of the wheels 50*a,b* defining a right side arc of movement between the solid lined and phantom lined positions of the lower plate 14 indicated by arrow A. FIG. 7 shows the wheels 50*a,b* set and locked for a left side arc of movement between the solid lined and phantom lined positions of the lower plate 14 indicated by arrow B. FIGS. 6 and 7 show how the stop pin 60 travels within the overlapping portions of the arcuate slots 56*a,b* such that movement of the lower plate 14 is stopped at the opposite ends 58 of the overlapping arcuate slots. From the foregoing it will be understood that the splint 10' with hinge 16' is fully ambidextrous and may be applied interchangeably on the inside or outside of the leg, and on either the left or right leg of the patient, to the same extent as the hinge 16 discussed in connection with FIGS. 2–5.

FIGS. 8 and 9 illustrate an optional feature of this invention, namely, a detent locking element in the form of screw 70 with a knurled knob 71 threaded into a through-hole 72 in detent 30. The detent locking screw 70 can be advanced to bear against the upper plate 12 with sufficient force to make a friction lock and hold the detent 30 in a retracted or engaged position. Optionally, a hole 74 may be provided in the upper plate 12 so that the threaded hole 72 aligns with hole 74 when the detent is retracted to a disengaged condition, and the detent locking screw 70 can then be advanced into hole 74 to hold the detent in a retracted position, as depicted in FIG. 9. Either way, the detent locking element 70 conveniently holds detent 30 away from engagement with the toothed wheels 50*a,b* for easier application of the splint to a patient's limb, so that the is splint can be quickly and easily bent to the angle of the patient's joint during fitting, and also to facilitate adjustment and positioning of the toothed wheels 50*a,b*, when setting the desired angular range of movement of the splint as described in the preceding paragraph.

Engagement of the detent locking screw 70 in hole 74 relieves the therapist from having to hold the detent against the urging of the bias spring 32 and frees both of his or her hands for the task of fitting the splint on the patient's limb with the detent retracted. This is desirable during installation of the splint so as to permit free movement of the hinge in order to match the angle of the splint plates to the position of the patient's joint being fitted with the splint. The angular adjustments of the hinge are more conveniently set after the splint is fitted to the patient's limb. The locking screw can also be subsequently used to secure the detent in engaged condition, if desired.

From the foregoing it will be appreciated that several advantages and improvements over previously known knee braces and splint have been disclosed. Although preferred embodiments have been described and illustrated for purposes of clarity and example it must be understood that many changes, modifications and substitutions will be apparent to those having only ordinary skill in this art without thereby departing from the scope of the invention as defined by the following claims.

The invention claimed is:

1. A hinge for an orthopedic splint comprising:
an upper plate and a lower plate connected for pivotal movement, a detent supported on said upper plate and displaceable into and out of an engaged condition thereby to lock the two plates against said pivotal movement in a selected angular relationship relative to each other, a spring normally urging said detent into said engagement, and a locking element removably engageable with said detent for holding said detent out of said engagement thereby to facilitate adjustment of the plates to a desired angular relationship.

2. The hinge of claim 1 wherein said locking element is threaded for engagement with said detent.

3. The hinge of claim 2 wherein said locking element is a screw engageable in a threaded screw hole defined in said detent, such that said screw engages said upper plate thereby to hold said detent in a disengaged condition against said urging of said spring.

4. The hinge of claim 3 wherein said screw is removable from the splint thereby to discourage tampering with the detent or may be left in place and tightened to secure said detent in said engaged condition.

5. The hinge of claim 1 wherein said locking element is a screw engageable in a threaded screw hole defined in said detent, wherein said screw can be threaded through said detent and into engagement against said upper plate thereby to hold said detent in a disengaged condition against said urging of said spring thereby to permit convenient angular adjustment of said hinge, and wherein said screw is removable from the splint thereby to discourage tampering with the detent or may be left in said screw hole in an untightened condition to serve as a finger hold for operating said detent.

6. A hinge for an orthopedic splint comprising:
an upper plate and a lower plate connected for pivotal movement, a pair of wheels turning concentrically with said pivotal movement of the plates, each of said wheels having a stop thereon operative for limiting pivotal movement of said lower plate relative to said upper plate in one direction of movement, such that the range of pivotal movement between the plates may be set by the angular spacing between the stops on said wheels, a tab extending radially from each of said wheels and a directional marking on each said tab as a visual indicator for assisting a therapist in setting the relative angular positions of the wheels during adjustment of the hinge, said directional markings being indicative of opposite directions of rotation of said wheels.

7. The hinge of claim 6 wherein said directional marking is a directional arrow on each of said tabs, said arrows pointing in opposite directions to each other.

8. A hinge for an orthopedic splint comprising:
an upper plate and a lower plate connected for pivotal movement, a detent supported on said upper plate and displaceable into and out of an engaged condition thereby to lock the two plates against said pivotal movement in a selected angular relationship relative to each other, a spring normally urging said detent into said engagement, cover means protecting said detent against displacement out of said engagement by an unaided hand, and an aperture in said cover means sized and disposed for admitting a tool end operative for displacing said detent out of said engagement against said urging of said spring and thus to free the plates for said pivotal movement, whereby tampering with the angular setting of said hinge by a patient wearing said orthopedic splint is discouraged.

9. The hinge of claim 8 wherein said detent is displaceable in a guide way defined between said upper plate and said cover means.

10. The hinge of claim 9 wherein said spring is contained in said guide way.

11. The hinge of claim 10 wherein said spring is a coil spring compressed between said upper plate and said detent.

12. The hinge of claim 8 wherein said detent is engageable with a toothed edge on said lower plate.

13. The hinge of claim 8 wherein said aperture is a slot aligned with a direction of displacement of said detent, said slot being sized and dimensioned to allow visual confirmation of engagement of said detent.

14. The hinge of claim 8 wherein said detent has a tool end receptacle adapted to receive the said tool end thereby to facilitate displacement of said detent by means of a said tool end.

15. The hinge of claim 8 wherein said pivotal movement comprises an arc including a zero angle position at an intermediate location along said arc, such that said plates may be moved through substantial angular ranges on either side of said zero angle position.

16. The hinge of claim 15 wherein said zero angle position is centered along said arc such that said plates may be pivoted through equal angular ranges on either side of said zero angle position.

17. The hinge of claim 16 wherein said plates are aligned in a straight line in said zero angle position.

18. The hinge of claim 8 further comprising a locking element removably engageable with said detent for holding said detent out of said engagement thereby to facilitate adjustment of the plates to a desired angular relationship.

19. The hinge of claim 18 wherein said locking element is threaded for engagement with said detent.

20. The hinge of claim 19 wherein said locking element is a screw engageable in a threaded screw hole defined in said detent, such that an end of said screw bears against said upper plate or engages with a hole in the upper plate thereby to hold said detent against said urging of said spring.

21. The hinge of claim 8 further comprising range setting means engageable by said detent, said range setting means being adjustable for limiting said pivotal movement to a greater or lesser arc in a disengaged condition of said detent.

22. The hinge of claim 21 wherein said range setting means comprises a pair of wheels turning concentrically with said pivotal movement of the plates, each of said wheels having a wheel edge engageable by said detent for locking the wheel relative to said upper plate, and a stop on each of said wheels operative for limiting pivotal movement of said lower plate relative to said upper plate in one direction of movement, a stop pin on said lower plate being disposed between the two stops such that the range of pivotal movement between the plates may be set by the angular spacing between the two stops when said detent is engaged for locking said wheels against rotation relative to said upper plate.

23. The hinge of claim 8 further comprising tabs projecting radially from said wheel edge of said wheels and directional markings on said tabs as a visual indicator for assisting a therapist in determining the relative positions of the tabs during adjustment of the hinge.

24. The hinge of claim 8 wherein said cover means includes a spacer mounted to said upper plate and defining a guide way for said detent and a cover plate for containing said detent in said guide way.

25. A hinge for an orthopedic splint comprising:
an upper plate and a lower plate connected for pivotal movement, a detent element supported on said upper plate and displaceable into and out of an engaged condition thereby to lock the two plates against said pivotal movement in a selected angular relationship relative to each other, a spring normally urging said detent into said engagement, wherein said pivotal movement comprises an arc including a zero angle position at an intermediate location along said arc, such that said plates may be moved through substantial angular ranges on either side of said zero angle position, and covering structure adjacent to said detent for substantially preventing access to said detent by an unaided hand and defining an aperture for admitting a tool operative for displacing said detent out of said engagement against said urging of said spring thereby to free the plates for said pivotal movement, such that tampering with the angular setting of said hinge by a patient wearing said orthopedic splint is discouraged.

26. The hinge of claim 25 wherein said zero angle position is centered along said arc such that said plates may be pivoted through equal angular ranges on either side of said zero angle position.

27. The hinge of claim 26 wherein said plates are aligned in a straight line in said zero angle position.

28. The hinge of claim 25 wherein said covering structure comprises an apertured plate generally encompassing said detent such that the detent is substantially recessed below an outer surface of said plate within said aperture, said aperture being sized to prevent operation of said detent by an unaided hand.

29. The hinge of claim 25 further comprising a locking element removably engageable with said detent for holding said detent out of said engagement thereby to facilitate adjustment of the plates to a desired angular relationship, said locking element also serving as a said tool for disengaging said detent against said spring urging.

30. The hinge of claim 29 wherein said locking element has a threaded end for engagement with said detent.

31. The hinge of claim 29 wherein said locking element is a screw engageable in a threaded screw hole defined in said detent to serve as a finger hold for operating said detent.

32. The hinge of claim 31 wherein said screw can be threaded through said detent and into engagement against said upper plate thereby to hold said detent in a disengaged condition against said urging of said spring thereby to permit convenient angular adjustment of said hinge.

33. A hinge for an orthopedic splint, comprising:
an upper plate and a lower plate connected for pivotal movement, a detent element supported on one of said plates and displaceable into and out of an engaged condition thereby to tock the two plates against said pivotal movement in a selected angular relationship relative to each other, and a spring normally urging said detent element into said engagement;
said detent element being shaped, arranged, and configured relative to a top surface on said one of said plates such as to substantially prevent retraction of said detent element from said engaged condition with a person's unaided hand; and
a finger hold element removably engageable with said detent element for assisting a therapist in disengaging said detent element against urging of said spring and is removable for discouraging actuation of said detent element by a patient fitted with said orthopedic splint, said finger hold element being also engageable with said one said plate for retaining said detent element out of said engaged condition.

34. The hinge as in claim 33 or wherein said detent element is linearly displaceable into and out of said engaged condition within a guideway provided on said one said plate.

35. A hinge for an orthopedic splint comprising:
an upper plate and a lower plate connected for pivotal movement, a pair of wheels turning concentrically with said pivotal movement of the plates, a detent supported on said upper plate, said detent movable into and out of engagement with a wheel edge on each of said wheels for locking said wheels against rotation relative to said upper plate, a stop on each of said wheels operative for limiting pivotal movement of said lower plate relative to said upper plate, a stop pin on said lower plate disposed between the stops on said wheels such that the range of pivotal movement between the upper and lower plates is determined by the angular spacing between the stops when said detent is engaged for locking said wheels against rotation relative to said upper plate, and said angular spacing is adjustable in a disengaged condition of said detent; and
a spring normally urging said detent into said engagement, and a finger hold element attached to said detent element for assisting a therapist in disengaging said detent element against the urging of said spring, said finger hold element being disengageable from said detent.

36. The hinge of claim 35 wherein said finger hold element is also engageable with said upper plate for retaining said detent element in a disengaged condition.

37. The hinge of claim 35 wherein said detent element is recessed relative to a top surface on said upper plate such as to substantially prevent retraction of said detent element from said engaged condition with a person's unaided hand in the absence of said disengageable finger hold element.

38. The hinge of claim 35 wherein said finger hold element is threaded for engagement into a threaded hole in said detent element.

39. The hinge of claim 35 further comprising cover means protecting said detent against displacement out of said engagement by an unaided hand, and an aperture in said cover means sized and disposed for admitting a tool end operative for displacing said detent out of said engagement against said urging of said spring and thus to free the plates for said pivotal movement, whereby tampering with the angular setting of said hinge by a patient wearing said orthopedic splint is discouraged.

40. A hinge for an orthopedic splint comprising:
upper and lower plates connected for pivotal movement about a pivot axis, a pair of wheels rotatable about said pivot axis including stop means for limiting said pivotal movement to a selected pivotal arc, a detent element supported on one said plate and displaceable into and out of an engaged condition with both said wheels for locking said wheels against rotation relative to said one said plate, and a spring normally urging said detent element into said engaged condition, said detent element being shaped, arranged, and configured to substantially prevent retraction of said detent element from said engaged condition with a person's unaided hand;
a finger hold element removably engageable with said detent element for assisting a therapist in disengaging said detent element against urging of said spring and is removable for discouraging actuation of said detent element by a patient fitted with said orthopedic splint;
said finger hold element being engageable with said one said plate for retaining said detent element in a disengaged condition.

41. The hinge of claim 40 wherein said detent element is linearly displaceable into and out of said engaged condition.

42. The hinge as in of claims 40 and 41 wherein said detent element is recessed relative to a top surface on said one said plate such as to substantially prevent retraction of said detent element from said engaged condition with a person's unaided hand.

43. The hinge as in claim 40 wherein said finger hold element is threaded for engagement into a threaded hole in said detent element.

44. A hinge for an orthopedic splint comprising:

an upper plate and a lower plate connected for pivotal movement, a detent element supported on said upper plate and displaceable into and out of an engaged condition thereby to lock the two plates against said pivotal movement in a selected angular relationship relative to each other, a spring normally urging said detent into said engagement, a pair of wheels turning concentrically with said pivotal movement of the plates, each of said wheels having a wheel edge engageable by said detent for locking the wheel relative to said upper plate, and a stop on each of said wheels operative for limiting pivotal movement of said lower plate relative to said upper plate in one direction of movement, a pin on said lower plate being disposed between the two stops such that the range of pivotal movement between the plates may be set by the angular spacing between the two stops when said detent is engaged for locking said wheels against rotation relative to said upper plate, a tab extending radially from each of said wheels and directional markings on each said tab indicative of opposite directions of rotation of said wheels as a visual indicator for assisting a therapist in setting the relative angular positions of the wheels during adjustment of the hinge.

45. The hinge of claim 44 wherein said directional markings are a directional arrow on each of said tabs, said arrows pointing in opposite directions to each other.

46. The hinge of claim 44 further comprising covering structure adjacent to said detent for substantially preventing access to said detent by an unaided hand and defining an aperture for admitting a tool into engagement with said detent for displacing said detent out of said engagement thereby to free the plates for said pivotal movement, such that tampering with the angular setting of said hinge by a patient wearing said orthopedic splint is discouraged.

47. The hinge of claim 46 wherein said covering structure comprises an apertured plate generally encompassing said detent such that the detent is substantially recessed below an outer surface of said plate within said aperture, said aperture being sized to prevent operation of said detent by an unaided hand.

48. A hinge for an orthopedic splint comprising:

an upper plate and a lower plate connected for pivotal movement, a detent element supported on said upper plate and displaceable into and out of an engaged condition thereby to lock the two plates against said pivotal movement in a selected angular relationship relative to each other, a spring normally urging said detent into said engagement, a pair of wheels turning concentrically with said pivotal movement of the plates, each of said wheels having a wheel edge engageable by said detent for locking the wheel relative to said upper plate, and a stop on each of said wheels operative for limiting pivotal movement of said lower plate relative to said upper plate in one direction of movement, a pin on said lower plate disposed for movement between the two stops such that the range of pivotal movement between the plates may be set by the angular spacing between the two stops when said detent is engaged for locking said wheels against rotation relative to said upper plate, and covering structure adjacent to said detent for substantially preventing access to said detent by an unaided hand and defining an aperture for admitting a tool operative for displacing said detent out of said engagement against said urging of said spring thereby to free the plates for said pivotal movement, such that tampering with the angular setting of said hinge by a patient wearing said orthopedic splint is discouraged.

49. The hinge of claim 48 further comprising a tab extending radially from each of said wheels and directional on each said tab markings as a visual indicator for assisting a therapist in setting the relative angular positions of the wheels during adjustment of the hinge.

50. The hinge of claim 49 wherein said directional markings are a directional arrow on each of said tabs.

* * * * *